United States Patent [19]

Laut et al.

[11] Patent Number: 5,645,648
[45] Date of Patent: Jul. 8, 1997

[54] PROCESS FOR CLEANING AND DISINFECTING DEVICES IN THE BREWING INDUSTRY

[75] Inventors: Bernhard Laut, Köln; Peter Mesters, Winterberg; Robert Rixen, Tönisforst, all of Germany

[73] Assignee: Karl Löffler GmbH & Company KG, Köln, Germany

[21] Appl. No.: 547,693

[22] Filed: Oct. 19, 1995

Related U.S. Application Data

[63] Continuation of Ser. No. 307,241, Sep. 16, 1994, abandoned.

[30] Foreign Application Priority Data

Sep. 21, 1993 [DE] Germany ............ 43 31 942.4

[51] Int. Cl.[6] ............ B08B 3/08; B08B 9/00; C23G 1/00; C23G 1/02
[52] U.S. Cl. ............ 134/2; 134/3; 134/22.14; 134/22.19
[58] Field of Search ............ 134/2, 3, 22.14, 134/22.19; 422/28, 37

[56] References Cited

U.S. PATENT DOCUMENTS 4,075,350 2/1978 Michaels .................... 424/316
4,857,225 8/1989 Terada et al. ............... 134/3

FOREIGN PATENT DOCUMENTS

| 253676 | 1/1988 | European Pat. Off. . |
| 404293 | 12/1990 | European Pat. Off. . |
| 2747355 | 10/1977 | Germany . |
| 3800337 | 1/1988 | Germany . |
| 1494109 | 12/1977 | United Kingdom . |
| 2255507 | 11/1992 | United Kingdom . |

*Primary Examiner*—Zeinab El-Arini
*Attorney, Agent, or Firm*—Keil & Weinkauf

[57] ABSTRACT

A method for cleaning and disinfecting articles in the brewing industry by applying to or at the contaminated place a composition containing 2 to 50% by weight of at least one compound having a peroxide group and/or a halocarboxylic acid;

1 to 25% by weight of at least one amine oxide derivative stable to oxidizing agents as surfactant foam booster component and remainder up to 100% water, the figures referring to total weight of the composition, and having a pH<7.

10 Claims, No Drawings

PROCESS FOR CLEANING AND DISINFECTING DEVICES IN THE BREWING INDUSTRY

This application is a continuation of application Ser. No. 08/307,241, filed on Sep. 16, 1994 and now abandoned.

BACKGROUND OF THE INVENTION

1. Field of the Invention

The present invention relates to a method for the cleaning and disinfection of articles and equipment such as vessels and conveyor belts in the brewing industry by applying an aqueous composition to or at the places to be cleaned.

2. Description of the Related Art

The cleaning and disinfection of articles of the type mentioned at the outset having relatively smooth inner surfaces which are used, e.g., in the area of packaging or charging foods or other perishable products is relatively problematical. It is not always possible, in the time available, to ensure a sufficiently long time of action of the corresponding components. This becomes disturbingly noticeable, e.g., very frequently in the brewing industry, in particular in the packaging area, if for example so-called beer spoilage organisms, which can multiply highly intensively under current conditions of low-oxygen packaging, are to be reliably eliminated. It has been shown, for example, that beer spoilage organisms such as *Pectinatus cerevisiiphilus* or *Megasphaera cerevisiae* have considerable resistance to the cleaning and disinfection agents currently used.

Although an absolutely satisfactory disinfection can be achieved with known disinfectants such as chlorine bleach solution, the use of this agent demonstrates undesirable effects on technical installations made of stainless steel such as pipes and the like as a consequence of corrosion phenomena. The legal restriction that waste water be allowed to contain no more than 0.2 mg of free chlorine per litre of waste water is likewise a disadvantage. At higher concentrations a separate treatment for waste water would have to be performed in order to decrease the concentration of equivalents of free chlorine below the prescribed value. Finally, it is known that chlorine bleach solution has a tendency to form so-called haloforms with organic compounds. These compounds are considered to be cancerogenic and are therefore also hazardous from the health aspect.

The disinfecting action of hydrogen peroxide or peracetic acid is known from first principles.

In order to ensure reliable disinfection at the concentrations of disinfectants conventionally used, a long contact time is required with such agents. However, this cannot be easily ensured as a result of the necessary high throughput of articles to be disinfected, in particular those having vertical relatively smooth surfaces.

Furthermore, the cleaning action of such a solution is not satisfactory.

EP-A-0,404,293 describes a thickened aqueous cleaning solution which has a bleaching action. The cleaning solution, in addition to the polymer used as thickener and a fluorescent brightener, contains $H_2O_2$ and defined amine oxides.

GB-A-2,255,507 likewise describes thickened, aqueous cleaning solutions which have a bleaching action. The solutions, in addition to a peroxo compound contain a dinonylphenylethoxylate as a thickener together with a micell-forming surfactant which can be an amine oxide.

DE-A-3,800,337 discloses an acidic cleaning agent for aluminum which has a pH of at most 2 and has, as constituents, a strong mineral acid selected from the group consisting of sulfuric acid, phosphoric acid and nitric acid, at least one peroxo compound and, as surfactant, an alkyldimethylamine oxide.

EP-A-253,676 discloses an aqueous, thickened cleaning solution which contains as thickener amine oxides. The solution further contains an acid salt or an acid which can be chloroacetic acid.

In DE-A-2,747,355, an antimicrobial composition is described which contains certain betaines, certain amine oxides and a protonating agent by which the pH is adjusted to between 4 and 5.5.

GB-B-1 4,494,109 teaches the composition of a bleaching surface-active composition which contains an addition product of $H_2O_2$ with a tertiary amine oxide and a peroxide activator.

SUMMARY OF THE INVENTION

The object of the present invention is to create a composition whose use avoids the disadvantages of known cleaning agents and disinfectants and permits articles and equipment having relatively smooth inner surfaces, such as containers and conveyor belts in the brewing sector, such as the packaging area of bottles or kegs, to be used, to be cleaned and to be disinfected. A simple method is to be created which permits the said inner surfaces of articles and equipment which come into contact with microbially perishable products to be reliably and reproducibly cleaned and disinfected.

This object is achieved by a method for cleaning and disinfecting articles and/or equipment, such as containers and/or conveyor belts in the brewing industry by applying to or at the contaminated places an aqueous composition containing 2 to 50% by weight of at least one compound having a peroxide group and/or a halocarboxylic acid;

1 to 25% by weight of at least one amine oxide derivative stable to oxidizing agents as surfactant foam booster component and remainder up to 100% water, the figures referring to total weight of the composition, and having a pH<7.

For a period of time dependent on the concentration of the constituents of the composition, the surfaces to be treated are brought into contact with the composition and then washed with water until the composition is removed. A contact time of 3 to 30 minutes is generally sufficient in order to achieve the desired cleaning and disinfecting action.

The aqueous composition (foam cleaner) used in the method is suitable in particular for use on vertical surfaces in order to ensure an adequate contact time of the cleaning and disinfecting composition, the surfactant foam booster component increasing the contact time of the disinfecting component, in particular on vertical smooth surfaces, in such a way that destruction of the bacteria which can cause microbial decomposition of the food to be charged into the container is ensured. To increase the disinfecting action and to remove mineral deposits it is advisable to add to the component containing a peroxide group and/or to at least one halocarboxylic acid and to the foam booster component (surface-active component) an acidulant, in order to adjust the pH of the aqueous composition to <7, preferably to pHs between 3 and 6.

Compounds containing a peroxide group which are useful are organic peroxides such as hydrogen peroxide or peroxosulfates. Organic peroxides, for example peroxy acids such as performic acid, peracetic acid or perbenzoic acid are suitable for use in the composition according to the invention. The concentration of the substance containing a peroxide group can be 2 to 50% by weight. If hydrogen peroxide is used, the concentration of this component is preferably 2 to 50% by weight, in each case based on weight of the composition which is directly contacted with the material to be cleaned and disinfected; a 70% strength $H_2O_2$ aqueous commercial product can be used as starting material which is appropriately diluted.

Halocarboxylic acids which can be used are, e.g., monobromoacetic, monochloroacetic and/or monoiodoacetic acid. The concentration of these acids in the composition to be used is about 1 to 6% by weight.

The foam booster component is a surface-active substance, preferably an amine oxide derivative, insensitive to oxidizing agents, in particular when compounds having a peroxide group are used. This has, in particular, a $C_9$- to $C_{20}$-alkyl chain. In a further preferred embodiment, the amine oxide can be a derivative of a trialkylamine having a $C_9$- to $C_{20}$-alkyl chain and two alkyl groups having a lower number of carbons, the latter types of substituents being able to have the same or different numbers of carbon atoms. The amine oxide component used is, in particular, a compound such as tallow-bis(2-hydroxyethyl)amine oxide, oleyl-bis(2-hydroxyethyl)amine oxide, coconut-bis(2-hydroxyethyl) amine oxide, coconutdimethylamine oxide. Fractionated coconut alkyl having a number of carbon atoms from 12 to 16 C atoms, tetradecyldimethylamine oxide and/or alkyldimethylamine oxides which have a number of carbon atoms from 12 to 18 in the alkyl chain are here preferred.

The concentration of the foam booster component, i.e. the surface-active substance insensitive to oxidation is preferably 1 to 25% by weight, based on the composition to be used.

The composition preferably has a pH of 3 to 6. The pH is established, for example, by organic acidulants such as mono-, di-, tri- and/or tetracarboxylic acids, if this pH range is not already present in the composition itself. Inorganic acidulants such as phosphoric acid are also suitable. However, hydroxycarboxylic acids such as citric acid or tartaric acid etc. can also be used.

The acids are used at a concentration of 5 to 25% by weight based on the finished composition.

The composition whose hydrogen peroxide content should be for example around 5% by weight can also be prepared shortly before use by dilution from an appropriately concentrated composition according to the invention. This is advantageous since the corresponding more highly concentrated compositions can be transported and stored with lower expense. The composition is adjusted to its concentration for use by conventional metering and dilution devices. It is equally possible to mix together the individual constituents briefly before use by means of a suitable metering device in order to obtain the composition according to the invention.

The invention is in particular a method for the cleaning and disinfection of articles and/or equipment such as containers and conveyor belts having relatively smooth inner surfaces in the brewing industry, the said articles and/or equipment being treated with an aqueous composition. The duration of the treatment is dependent on the concentration of the individual components. The time of action can typically be 3 min to 30 min. The temperatures used during the disinfection and cleaning process are between 5° C. and 35° C., a range between 15° C. and 25° C. being preferred. After the appropriate time of action, the treated articles and equipment such as containers and conveyor belts are washed until the composition is removed. Washing is carried out with standard mains water which is generally sufficiently sterile in order to retain to a sufficient extent the sterility of the disinfected apparatuses and containers.

DESCRIPTION OF THE PREFERRED EMBODIMENTS

The compositions can be brought into contact with the containers to be cleaned and disinfected by commercial foaming apparatuses. The method according to the invention using the aqueous composition is suitable in particular for making beer-spoilage microorganisms such as *Pectinatus cerevisiiphilus* and/or *Megasphaera cerevisiae* harmless.

The invention is now described on the basis of the following examples:

EXAMPLE 1

A cleaning composition is prepared from the following substances:

53% by weight of water,
35% by weight of citric acid,
7% by weight of hydrogen peroxide and
5% by weight of coconutalkyldimethylamine oxide For homogeneous mixing, the mixture is gently stirred during preparation. After being charged into a commercial pressurized foam apparatus, the composition is used for the cleaning and disinfection of containers, conveyor belts and equipment. The time of action is 15 min at 20° C. Articles and equipment are then washed with clear water. A complete cleaning of the articles is achieved as is a disinfection rate which ensures an outstanding storage life of the packaged product, for example beer.

EXAMPLE 2

A cleaning composition is prepared from the following substances:

65% by weight of water,
20% by weight of citric acid,
12% by weight of hydrogen peroxide and
3% by weight of coconutalkyldimethylamine oxide For homogeneous mixing, the mixture is gently stirred during preparation. After charging into a commercial pressurized foam apparatus, the composition is used for the cleaning and disinfection of containers, conveyor belts and equipment. The time of action is 15 min at 20° C. Articles and equipment are then washed with clear water. A complete cleaning of the articles is achieved as is a disinfection rate which ensures an outstanding storage life of the packaged product, for example beer.

EXAMPLE 3

A cleaning composition is prepared from the following substances:

70% by weight of water,
20% by weight of citric acid,
5% by weight of monobromoacetic acid and
5% by weight of coconutalkyldimethylamine oxide For homogeneous mixing, the mixture is gently stirred during preparation. After charging into a commercial pressurized foam apparatus, the composition is used for the cleaning and disinfection of containers, conveyor belts and equipment. The time of action is 10 min at 20° C. Articles and equipment are then washed with clear water. A complete cleaning of the articles is achieved as is a disinfection rate which ensures an outstanding storage life of the packaged product, for example beer.

EXAMPLE 4

A cleaning composition is prepared from the following substances:

53% by weight of water,

12% by weight of acetic acid,

2% by weight of phosphoric acid,

30% by weight of hydrogen peroxide and

3% by weight of coconutalkyldimethylamine oxide

For homogeneous mixing, the mixture is gently stirred during preparation. After charging into a commercial pressurized foam apparatus, the composition is used for the cleaning and disinfection of containers, conveyor belts and equipment. The time of action is 15 min at 20° C. Articles and equipment are then washed with clear water. A complete cleaning of the articles is achieved as is a disinfection rate which ensures an outstanding storage life of the packaged product, for example beer.

EXAMPLE 5

A cleaning composition is prepared from the following substances:

35% by weight of water,

10% by weight of citric acid,

15% by weight of acetic acid

35% by weight of hydrogen peroxide and

5% by weight of coconutalkyldimethylamine oxide

For homogeneous mixing, the mixture is gently stirred during preparation. After charging into a commercial pressurized foam apparatus, the composition is used for the cleaning and disinfection of containers, conveyor belts and equipment. The time of action is 15 min at 25° C. Articles and equipment are then washed with clear water. A complete cleaning of the articles is achieved as is a disinfection rate which ensures an outstanding storage life of the packaged product, for example beer.

EXAMPLE 6

A cleaning composition is prepared from the following substances:

37% by weight of water,

30% by weight of citric acid,

30% by weight of hydrogen peroxide and

3% by weight of oleyldimethylamine oxide

For homogeneous mixing, the mixture is gently stirred during preparation. After charging into a commercial pressurized foam apparatus, the composition is used for the cleaning and disinfection of containers, conveyor belts and equipment. The time of action is 15 min at 25° C. Articles and equipment are then washed with clear water. A complete cleaning of the articles is achieved as is a disinfection rate which ensures an outstanding storage life of the packaged product, for example beer.

We claim:

1. A method for cleaning and disinfecting brewing equipment comprising the following steps:

(a) preparing an aqueous cleaning composition containing 2 to 50% by weight of at least one disinfecting compound having a peroxide group and a halocarboxylic acid;

1 to 25% by weight of at least one amine oxide compound stable to oxidizing agents as a surfactant foam booster component;

a remainder of up to 100% water;

(b) charging said aqueous cleaning composition into a pressurized foam apparatus, thereby forming a foam cleaner; and (c) applying said foam cleaner to a contaminated surface to clean and disinfect said surface.

2. The method as claimed in claim 1, wherein, in the aqueous cleaning composition, the compound having a peroxide group is an inorganic peroxide or an organic peroxide or a mixture of an inorganic peroxide and an organic peroxide.

3. The method as claimed in claim 1, wherein, in the aqueous cleaning composition, the halocarboxylic acid is monochloroacetic, monobromoacetic or monoiodoacetic acid or a mixture of monochloroacetic, monobromoacetic and monoiodoacetic acids.

4. The method as claimed in claim 1, wherein a combination of a compound containing a peroxide group and a halocarboxylic acid is contained in the foam cleaner.

5. The method as claimed in claim 1, wherein, in the foam cleaner, the amine oxide derivative is a trialkylamine oxide having a $C_8$–$C_{20}$-alkyl chain and two alkyl groups having a lower number of carbon atoms in the alkyl chain which can be identical or different.

6. The method as claimed in claim 5, wherein the amine oxide is tallow-bis(2-hydroxyethyl)amine oxide, oleyl-bis (2-hydroxyethyl)amine oxide, coconut-bis(2-hydroxyethyl) amine oxide, coconutdimethylamine oxide, tetradecyldimethylamine oxide and alkyldimethylamine oxides which have 12 to 18 carbon atoms in the alkyl chain.

7. The method as claimed in claim 1, wherein the pH of the foam cleaner is 3 to 6.

8. The method as claimed in claim 1, wherein the aqueous cleaning composition contains phosphoric acid, organic mono-, di-, tri- and tetracarboxylic acids and hydroxycarboxylic acids.

9. The method as claimed in claim 1 for the cleaning and disinfection of articles, equipment and containers having smooth surfaces by contacting the surfaces with the foam cleaner for a time sufficient for achieving disinfection and cleaning and subsequent washing with water until the foam cleaner is removed.

10. The method as claimed in claim 9, wherein the time of action of the foam cleaner on the surfaces to be treated is 3 to 30 minutes.

* * * * *